United States Patent
Bora

(10) Patent No.: US 10,357,672 B2
(45) Date of Patent: Jul. 23, 2019

(54) APPARATUS, SYSTEM AND METHOD TO PREVENT FOGGING OF EYEWEAR

(71) Applicant: Navin Raj Bora, Chicago, IL (US)

(72) Inventor: Navin Raj Bora, Chicago, IL (US)

(*) Notice: Subject to any disclaimer, the term of this patent is extended or adjusted under 35 U.S.C. 154(b) by 257 days.

(21) Appl. No.: 15/226,013

(22) Filed: Aug. 2, 2016

(65) Prior Publication Data

US 2018/0036563 A1 Feb. 8, 2018

(51) Int. Cl.
*A61F 9/02* (2006.01)
*A62B 18/08* (2006.01)
*A62B 23/02* (2006.01)

(52) U.S. Cl.
CPC ............ *A62B 18/084* (2013.01); *A61F 9/028* (2013.01); *A61F 9/029* (2013.01); *A62B 23/025* (2013.01)

(58) Field of Classification Search
CPC ... A62B 18/082; A62B 18/084; A62B 23/025; A41D 13/11; A41D 13/1184
USPC ..................................................... 128/206.19
See application file for complete search history.

(56) References Cited

U.S. PATENT DOCUMENTS

| | | | |
|---|---|---|---|
| 2,669,717 A | 2/1954 | Diggs | |
| 3,834,384 A | 9/1974 | Raines | |
| 3,888,246 A | 6/1975 | Lauer | |
| 3,890,966 A * | 6/1975 | Aspelin | A41D 13/1115 128/201.17 |
| 3,974,829 A | 8/1976 | Tate, Jr. | |
| 4,037,593 A * | 7/1977 | Tate, Jr. | A41D 13/1115 128/201.17 |
| 4,250,577 A * | 2/1981 | Smith | A61F 9/029 2/427 |
| 4,384,577 A | 5/1983 | Huber et al. | |
| 4,419,993 A * | 12/1983 | Petersen | A41D 13/1123 128/201.15 |
| 4,796,621 A * | 1/1989 | Barle | A41D 13/1146 128/206.19 |
| 4,944,039 A * | 7/1990 | Dietrich | A41D 13/11 2/13 |
| 5,020,533 A * | 6/1991 | Hubbard | A41D 13/1115 128/201.15 |
| 5,419,318 A * | 5/1995 | Tayebi | A41D 13/1146 128/205.27 |
| 5,584,078 A | 12/1996 | Saboory | |
| 5,682,879 A * | 11/1997 | Bowers | A41D 13/1115 128/201.12 |
| 5,694,925 A * | 12/1997 | Reese | A41D 13/1115 128/206.19 |
| 5,701,892 A | 12/1997 | Bledstein | |
| 5,797,146 A | 8/1998 | Matich | |
| 6,354,296 B1 | 3/2002 | Baumann et al. | |

(Continued)

*Primary Examiner* — Kristen Matter
(74) *Attorney, Agent, or Firm* — Cherskov, Flaynik & Gurda, LLC

(57) ABSTRACT

An apparatus, system and method to prevent fogging of glasses worn by a wearer has a mask made from a filtration material. The mask has a left side and a right side. A strap extends from the mask to hold the mask in position on the wearer. A vent is positioned on both the left side and the right side of the mask, in one version. An adhesive foam layer extends across the mask and the strap to attach the mask to the glasses. Arms may extend from the glasses toward ears of the wearer. The adhesive foam layer attaches the mask to the arms of the glasses. A flap extends from the foam layer. Pulling the flap removes the adhesive foam layer from the glasses.

20 Claims, 3 Drawing Sheets

(56) References Cited

U.S. PATENT DOCUMENTS

| | | | |
|---|---|---|---|
| 6,520,181 B2 | 2/2003 | Baumann et al. | |
| 6,988,500 B1 | 1/2006 | Cox | |
| 7,077,137 B2 | 7/2006 | Russell | |
| 7,077,140 B1 | 7/2006 | Berke | |
| 7,475,982 B2 * | 1/2009 | Welchel | A41D 13/1184 |
| | | | 351/158 |
| 7,488,068 B2 | 2/2009 | Welchel et al. | |
| 7,703,456 B2 * | 4/2010 | Yahiaoui | A41D 13/1184 |
| | | | 128/206.19 |
| 7,861,317 B2 | 1/2011 | Beliveau | |
| 8,240,302 B1 | 8/2012 | Tayebi et al. | |
| 8,387,163 B2 | 3/2013 | Beliveau | |
| 8,857,433 B1 | 10/2014 | Kelly | |
| 2002/0056450 A1 | 5/2002 | Lee | |
| 2003/0035082 A1 * | 2/2003 | Olney | A61F 9/026 |
| | | | 351/62 |
| 2004/0237962 A1 * | 12/2004 | Russell | A41D 13/1184 |
| | | | 128/201.17 |
| 2007/0252946 A1 * | 11/2007 | Welchel | A41D 13/1184 |
| | | | 351/62 |
| 2014/0196187 A1 | 7/2014 | Beliveau | |
| 2014/0196200 A1 | 7/2014 | Beliveau | |
| 2015/0351468 A9 | 12/2015 | Chinquee | |
| 2016/0016021 A1 | 1/2016 | Duffy | |

* cited by examiner

APPARATUS, SYSTEM AND METHOD TO PREVENT FOGGING OF EYEWEAR

TECHNICAL FIELD

The present disclosure relates to a face mask, such as a protective and/or hygienic face mask, adapted for engagement with eyewear, such as sunglasses. More particularly, a foam layer attaches the face mask to the eyewear to substantially prevent or eliminate fogging of interior-facing lens surfaces of the eyewear by directing air exhaled by a wearer out through vents positioned on each side of the face mask. The foam layer adheres a lower frame portion of the sunglasses, and/or the arms of the sunglasses, to the face mask, forming a substantially impermeable barrier against bacteriological contaminants prevalent in the atmosphere. Therefore, air exhaled by the wearer is effectively directed away from both the face mask and the sunglasses while the wearer is still protected against exterior contaminants by the face mask.

BACKGROUND

Cities and other heavily urbanized areas may experience considerable human congestion at various locations around the world due to high human density. Therefore, public transportation mediums seeking to address the movement needs of local populations are often run at maximum capacity. As a result, individual passengers on subway train cars may be forced to be in physical contact with each other as the train travels to its next stop. Given that infectious disease, bacteria, allergens and/or other undesirable human-produced biologic material may easily spread in such high-density environments, many passengers choose to proactively wear protective hygienic face masks, like those used by surgeons and other medical professionals in an operating room, to guard against inhaling undesirable biologic material expelled by nearby passengers (e.g., through sneezing or coughing), and/or environmental-related contaminants (e.g., smoke, other forms of industrial air pollution and particulate matter).

However, such readily-available and mass-produced face masks may not be suitably equipped to attach, adhere, and/or otherwise combine the body of the face mask with eyewear, such as sunglasses. Thus, wearing sunglasses in combination with traditional face masks may require a wearer or user to choose whether to place the lenses of the sunglasses above the face mask, or to pull the face mask above the lenses, to form an interface between the lenses of the sunglasses and the face mask.

Choosing to pull the face mask above the lenses results in obscuring the wearer's line of vision through the sunglasses, which is an undesirable result. The remaining option, positioning the sunglasses on and/or above the face mask results in warm and moist exhaled air rising through the face mask upon exhalation by the user to coat the interior-facing lens surfaces of the sunglasses. Such surfaces allow the warm and moist exhaled air to condense thereon, resulting in the undesirable fogging up of the surfaces, also obscuring the wearers line of vision through the sunglasses.

Thus, there is a need for a comfortable, relatively inexpensive, readily-available surgical-type hygienic face mask adapted to combine and/or attach easily (i.e., via a foam layer that may have an adhesive associated therewith, or via the application of a removable semi-viscous liquid/gel coating between the face mask and the sunglasses) with sunglasses, of a variety of shapes and/or styles. The face mask may be oriented and combined with the eyewear such that exhaled air from the nostrils may be preferentially directed outwards through vents located on each side of the face mask, rather than rising upward to fog up and thus obscure vision through the interior-facing lens surfaces of the sunglasses. Furthermore, such a face mask should remain in a fixed position relative to a wearer's face, permitting for the wearer to freely turn and/or move his or her head while, for example commuting in a public train and/or bus to read material carried in hand.

SUMMARY

The present disclosure relates to a face mask adapted for use with eyewear, such as sunglasses, to prevent fogging of an interior-facing lens surfaces of the eyewear. More specifically, the face mask has a foam layer spread across a top region of the face mask intended to adhere to a lower frame portion of the sunglasses, as well as, in some embodiments, arms extending from the sunglasses, towards the ears of a wearer of the face mask and sunglasses.

In an embodiment, an apparatus to prevent fogging of glasses worn by a wearer has a mask made from a filtration material. The mask may have a first side and a second side. A strap may extend from the mask to hold the mask in a position on the wearer. A vent may be located on each side. A foam layer may extend across the mask and the strap to attach the mask to the glasses, which have arms that are configured to extend from the glasses toward ears of the wearer such that the foam layer attaches the mask to the arms of the glasses.

Further, in an embodiment, a system to direct air exhaled by a user away from glasses worn by the user has a mask contoured to conform to facial features of the user. The mask may have a filtration membrane and may be defined by a pair of sides connected by a top and a bottom. A securing strap may secure the mask to the user. A pair of mesh ports are on the mask, where each mesh port of the pair of mesh ports is located adjacent to each side of the pair of sides of the mask. The mesh ports may direct air exhaled by the user away from the mask. A barrier may be between the top of the mask and glasses worn by the user. The barrier may form a seal between the mask and the glasses to prevent air exhaled by the user from fogging the glasses.

Moreover, in an embodiment, a method for using a face mask involves securing the face mask against glasses worn by a wearer. The face mask may be positioned on the wearer. Straps of the face mask may be extended around the wearer. An adhesive foam layer of the face mask may be adhered on the glasses and arms extending from the glasses toward ears of the wearer. The face mask may be secured against the glasses.

An advantage of the present disclosure is to provide a face mask with vents, each vent of the vents being positioned adjacent to a first side and a second side of the face mask such that air exhaled from the user of the face mask may be directed outwards through the vents instead of rising to fog up the interior-facing lens surfaces of sunglasses worn with the face mask.

Another advantage of the present disclosure is to provide a face mask where a density level of intertwined fibers defining vents positioned on each a first and second side of the face mask is selected at least partially based on a respiration rate of a wearer, such that the density level of intertwined fibers for face mask applications involving rapid respiration may be relatively looser or less concentrated, and vice-versa for conditions involving slow respiration.

Yet another advantage of the present disclosure is to provide a face mask that may be positioned for placement on a face of a wearer between a first and second mode such that the first mode places the face mask closer to an ear of the user, and where the second mode places the face mask further away from the ear of the wearer.

Still another advantage of the present disclosure is to provide a face mask with a foam layer formed above and in contact with the top of the face mask, such that the foam layer extends across the first side to a second side of the face mask and along a securing strap of the face mask to contact and to adhere to arms of the eyewear.

Still further another advantage of the present disclosure is to provide a face mask with a foam layer that reversibly deforms to provide cushioning against eyewear positioned adjacent to the face mask.

Additional features and advantages of the present disclosure are described in, and will be apparent from, the detailed description and from the drawings.

BRIEF DESCRIPTION OF THE DRAWINGS

The foregoing and other purposes, features and aspects of the disclosure will become apparent from the following detailed description of embodiments, given by way of illustration and not limitation with reference to the accompanying drawings, in which.

DETAILED DESCRIPTION

The present disclosure generally relates to a face mask adapted for use with eyewear, such as sunglasses, to prevent against the fogging of interior-facing lens surfaces of the eyewear. More specifically, the face mask has a foam layer spread across a top region of the mask to adhere the face mask to a lower frame portion of the sunglasses, as well as, in an embodiment, to the arms of the sunglasses, to at least substantially form a seal preventing bacteriological contaminants, or other pollutants, from traveling through the face mask to be breathed in by a wearer. Vents are located on opposing sides of the face mask to direct air exhaled by the wearer there-through, effectively preventing for the rising of the warm and moist exhaled air upward to fog up the interior-facing lens surfaces of the sunglasses, allowing for continued unimpeded vision through the sunglasses.

Figure 1:
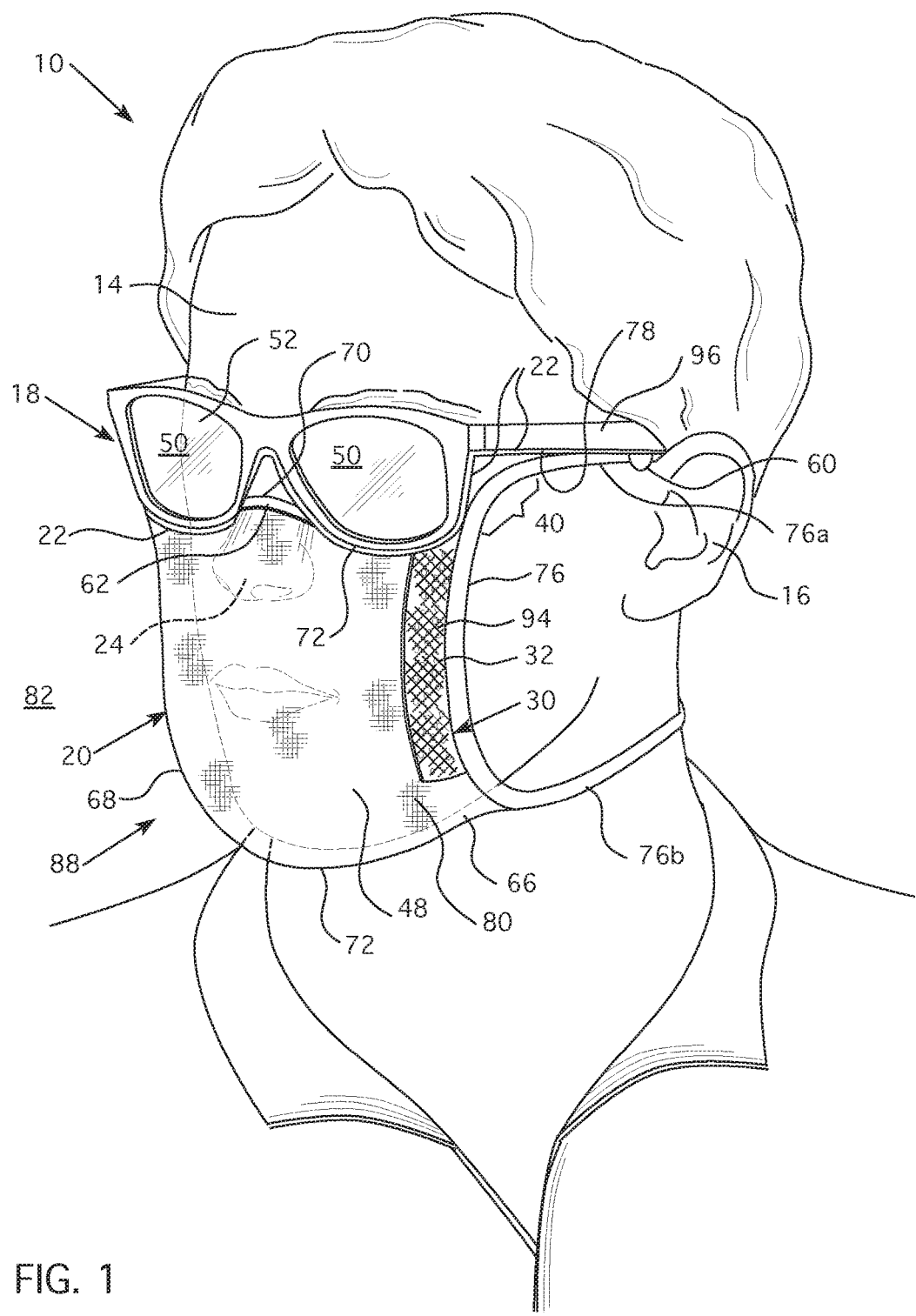
FIG. 1 illustrates a perspective view of the face mask adapted for use with eyewear, such as sunglasses, to prevent fogging of the interior-facing lens surfaces of the sunglasses.

Referring to FIG. 1, removable eyewear, such as a pair of sunglasses 18, are shown as worn on a wearer 10. A face mask 20 configured to prevent fogging of interior-facing lens surfaces 50 of the sunglasses 18 may be worn in combination with the sunglasses 18 as shown, e.g., in situations where both protection from sunlight and exposure to harmful environmental conditions is desired. The face mask 20 may have a main body 48 that is pliable and able to be contoured to accommodate facial features of the wearer 10, such as his or her cheekbones, nose, lips, and/or mouth. The face mask 20 may be rectangular and be defined by a first, e.g., "right" side 66 and a second, e.g., "left" side 68 positioned parallel and opposite to the right side 66. Relative definitions of "right" and "left", when used to describe the first and second sides 66 and 68, respectively, are from the vantage point of looking at the wearer 10. One skilled in the art will appreciate that other different orientations and/or configurations of "right" and "left" may be from the vantage point of the wearer 10, for example, without departing from the scope and spirit of the present disclosure. Further, the face mask 20 may have a top 70 and a bottom 72 that is positioned parallel and opposite to the top 70, where the top and bottom 70 and 72, respectively, may together be connected by a pliable contour region 40 of the face mask 20. In an embodiment, an uppermost portion of the contour region 40 may compress against the sunglasses 18 and arms 96 extending outwardly there-from to form a substantially air-tight seal (not shown in the FIGS.) with the sunglasses 18 to prevent against the passage of contaminants exterior to the face mask 20 into the orifices of, for example, the nose and mouth of the wearer 10. A foam layer 22, made from, for example, soft closed cell foam may be positioned between the top 70 of the face mask 20 and the sunglasses 18, and extend from the first side 66 to the second side 68 of the face mask 20. In an embodiment, the foam layer 22 may be substantially constructed from or otherwise include an adhesive material or layer 78 suitable for joining plastic, acetate, and/or various types of cloth, including felt, to removably adhere the face mask 20 to the sunglasses 18 and the arms 96 extending there-from. The foam layer 22 may also at least partially extend along a securing strap 76 to contact and to adhere to arms 96 of the sunglasses 18. As shown in FIG. 1, each arm 96 of the sunglasses 18 may be configured to affix onto an ear 16 of the wearer 10.

Figure 2:
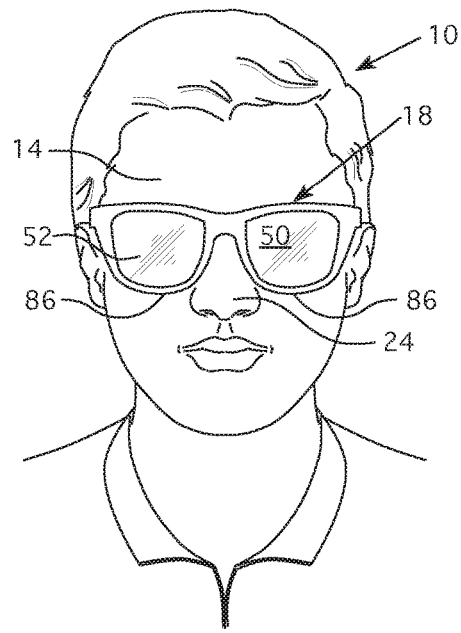
FIG. 2 illustrates a front view of a person wearing sunglasses.

In detail, the foam layer 22 may reversibly compress and/or otherwise deform to fit against a lower frame portion 86, as shown in FIG. 2, of the sunglasses 18 to at least partially define or form the contour region 40 across facial features of the wearer 10. An adhesive layer 78 of, on or otherwise associated with the foam layer 22 may adhere the face mask 20 to the sunglasses 18. Moreover, the foam layer 22 may attach to the securing strap 76 by the adhesive layer 78 to the arms 96 of the sunglasses 18 to hold the face mask 20 against a face 14 of the wearer 10.

The adhesive layer 78 in combination with the foam layer 22 may substantially hold the face mask 20 against the sunglasses 18 to define the contour region 40 relative to the face 14 of the wearer 10 to effectively seal off the face mask 20 from the sunglasses 18, preventing warm and moist air exhaled by the wearer 10 from rising upward to fog the interior-facing lens surfaces 50 of the sunglasses 18. Accordingly, any and/or all vapor, air and/or moisture associated with human breath exhaled by the wearer 10 may be at least partially directed through a filtration membrane 80 on the main body 48 of the face mask 20. The remaining air may partially pass through any gaps between the face mask 20 and the sunglasses 18 along the contour region 40 due to gaps therein, but otherwise pass primarily through a pair of vents 30, where each vent of the pair of vents 30 may be positioned adjacent to each the first and second sides 66 and 68, respectively, of the face mask 20 as shown in FIG. 1.

Each vent of the pair of vents 30 may be include a mesh 32 extending across each vent as shown in FIG. 1. The mesh 32 may be defined by woven, intersecting, and/or otherwise intertwined fibers 94 at various density levels. For example, the density, or concentration, level of the fibers 94 weaved across each vent of the vents 30 may be selected as being representative, proportional to, or otherwise based on an expected respiratory frequency, volume and/or rate of the wearer 10. Specifically, the wearer 10 may desire to use the face mask 20 in a high human density and low activity environment such as a subway train car, for example. For use in such an environment, the face mask 20 may be selected and/or configured to include vents 30 with the mesh 32 having the fibers 94 intertwined at a relatively high density or concentration level. Since the wearer 10 may expect to be standing, with minimal movement, for an extended period, his or her respiration and/or frequency of breathing may be at a standard resting rate. Therefore, easy breathability through the vents 30 of the face mask 20 may not be needed in such a dormant environment, e.g., where the wearer 10 is merely standing in a subway car, where the high density or concentration of the intertwined fibers 94 defining the mesh 32 may effectively provide maximum blockage and/or protection to the wearer 10 against the permeation and entrance of undesirable particulate matter and/or biological contaminants prevalent in an exterior atmosphere 82 through the vents 30. Alternatively, should the wearer 10 intend to wear the face mask 20 in a high-intensity and movement (but low human density) environment, such as a soccer field and/or pitch, for example, then fewer intertwined fibers 94 may be used to form the mesh 32, resulting in the mesh 32 having a relatively high breathability when compared to the subway train car environment example described earlier.

As shown in FIG. 1, in an embodiment, the top 70 and the bottom 72 of the face mask 20 may connect the first side 66 to the second side 68 to generally define the face mask 20 as being shaped as a rectangle. One skilled in the art will appreciate that other variations in shapes, sizes, and/or orientations of the face mask 20 may exist without departing from the scope and spirit of the present disclosure. The main body 48 may be constructed by or otherwise include the filtration membrane 80 disposed on or within the main body 48, where securing strap 76 extends from the main body 48 to secure the face mask 20 on the wearer 10 by affixing to the ears 16. Therefore, the securing strap 76 retains the face mask 20 substantially on the face 14 of the wearer 10 allowing for the wearer 10 to breathe through his or her nose 24 to inhale air from the exterior atmosphere 82 through the face mask 20. Likewise, the pair of vents 30 are positioned adjacent to each the first and second sides 66 and 68, respectively, of the face mask 20 to permit for fluid communication between the wearer 10 and the environment 82, e.g., such that the wearer 10 may exhale air directed through vents 30 to avoid rising upward to fog up the interior-facing lens surfaces 50 of the sunglasses 18.

In an embodiment, the face mask 20, as substantially described above, when used in combination with the sunglasses 18 to prevent the fogging of the interior-facing lens surfaces 50 may be alternatively described as a system 88, also shown by FIG. 1, provided to direct air exhaled by the wearer 10, who may also be referred to as a user 10, away from his or her eyes. The system 88 also includes the face mask 20 with a main body 48 that is contoured to conform to the wearer 10. The main body 48 has the filtration membrane 80, which may be particularly adapted to trap biologic materials, thus effectively preventing their passage there-through. Moreover, depending on a desired configuration of the pair of vents 30, the mesh 32 selected to span across each vent of the pair of vents 30 may include fibers 94 intertwined at a density or concentration level sufficient to prevent contaminants prevalent in the exterior atmosphere 82 from passing through the filtration membrane 80. The main body 48 may be defined in shape by the first side 66 and the second side 68 that are connected by the top 70 and the bottom 72, and the securing strap 76 secures the main body 48 of the face mask 20 to the wearer 10 by affixing to the ears 16 as shown in FIG. 1. Each vent of the pair of vents 30 is located adjacent to each the first and second sides 66 and 68, respectively, in between the top 70 and the bottom 72. One skilled in the art will appreciate that the pair of vents 30 may be alternatively be referred to as mesh ports. The mesh 32 extending across each vent of the pair of vents 30 may include perforations 34 (not shown in the FIGS.) to assist in directing air exhaled by the wearer 10 out of the face mask 20 toward the exterior atmosphere 82.

As described earlier, the foam layer 22 may reversibly compress and/or deform to fit against the lower frame portion 86, as shown in FIG. 2, of the sunglasses 18 to form the contour region 40. In an embodiment, the contour region 40 may be alternatively referred to as an adhesive vapor barrier attachment, or as a barrier, being positioned generally between the top 70 of the face mask 20 and sunglasses 18 worn by the user, to both cushion the face mask 20 against the sunglasses 18 as well as to removably attach the two, e.g., to attach the face mask 20 to the sunglasses 18. Therefore, the vapor barrier attachment may form a sealed layer between the main body 48 of the face mask 20, the sunglasses 18, and the face 14 of the wearer 10 to prevent air exhaled by the wearer 10 from rising upward to contact and/or collect on the interior-facing lens surfaces 50 of the sunglasses 18. Air may otherwise be directed through the mesh 32 of the pair of vents 30 to escape the main body 48 of the face mask 20 to enter the exterior atmosphere 82. Moreover, in an embodiment, the permeability of the filtration membrane 80 used to form the main body 48 may be selected in view of the intended respiration rate of the user.

As shown in FIG. 1, a flap or tab 60 may extend from the foam layer 22 attaching the securing strap 76 to each of the arms 96 of the sunglasses 18. The tab 60 may be pulled outwards and/or otherwise away from each arm 96 to remove the foam layer 22 from the arms 96. Accordingly, the face mask 20 may be removed from the sunglasses 18.

Further, in an embodiment, a binding or flexible ridge 62 may extend lengthwise across the nose 24 of the wearer 10 on the main body 48 of the face mask 20. Squeezing, positioning, conforming or any other type of adjustment of the flexible ridge 62 may assist in conforming the main body 48 of the face mask 20 to the nose 24 of the wearer 10. The securing strap 76 may be defined in greater detail as including a top strap 76a and a bottom strap 76b connected there-to. The top strap 76a may extend toward the ear 16 and the bottom strap 76b may extend from the bottom 72 to connect with the top strap 76a behind the ear 16 of the wearer 10. Also, in an embodiment, the foam layer 22 may also provide cushioning and protection to the wearer 10 from unwanted movement of the sunglasses 18 onto the main body 48 of the face mask 20.

Referring to FIG. 2, a front view of the sunglasses 18 as worn on the face 14 of the wearer 10 is shown. In an embodiment, the wearer 10 may position the sunglasses 18 on his or her face 14 prior to wearing the face mask 20 to ensure a proper line of sight through both the interior-facing lens surfaces 50 and exterior-facing lens surfaces 52. As shown in FIG. 2, the lower frame portion 86 of the sunglasses 18 may feature no special coating, glue and/or other adhesive that may interfere with the application of the adhesive layer 78 on, around, or otherwise associated with the foam layer 22 to attach and/or remove the face mask 20 to and/or from the sunglasses 18.

Figure 3:
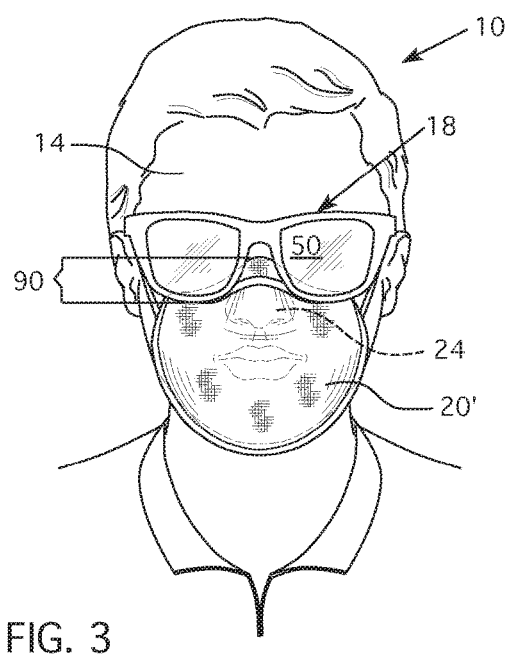
FIG. 3 illustrates a front view of a person wearing sunglasses overlapping the face mask.

Referring to FIG. 3, a front view of the wearer 10 wearing the sunglasses 18 above and/or on top of a conventional face mask 20' is shown. The conventional face mask 20' may not include the contour region 40, as shown in FIG. 1, for example, and may instead feature an overlap region 90. The sunglasses 18 may be placed over the conventional face mask 20' in the overlap region 90 to therefore allow vapor, air, and/or moisture-laden breath exhaled by the wearer 10 through the conventional face mask 20' to rise upwardly through the gap between the conventional face mask 20' and the sunglasses 18 to coat the interior-facing lens surfaces 50 to thus obscure and/or otherwise interfere with vision through the sunglasses 18. Alternatively, placing the conventional face mask 20' over the sunglasses 18 in the overlap region 90 still fails to address issues related to the fogging up of the interior-facing lens surfaces 50 of the sunglasses 18, and may actually enhance the deposition of moisture from exhaled air or breath thereon by allowing exhaled air to rise directly from the nose 24 of the wearer 10 onto both the exterior-facing lens surfaces 52 and the interior facing lens surfaces 50 of the sunglasses 18.

Figure 4:
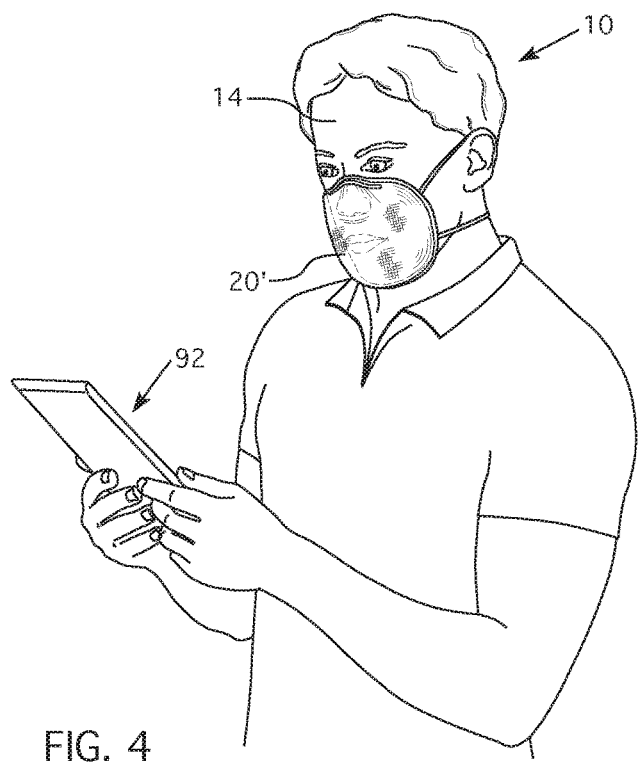
FIG. 4 illustrates a perspective view of a person wearing the face mask while reading and/or using an electronic peripheral.

Referring to FIG. 4, the wearer 10 is shown wearing only the conventional face mask 20' without the sunglasses 18 to read an electronic peripheral 92, such as an e-book or tablet computer. The wearer 10, for example may hold an electronic peripheral 92, such as an e-book, for example, close to the wearer 10. Accordingly, the wearer 10 may easily read and/or view material on the e-book while standing in a crowded environment, such as on a subway train.

Figure 5:
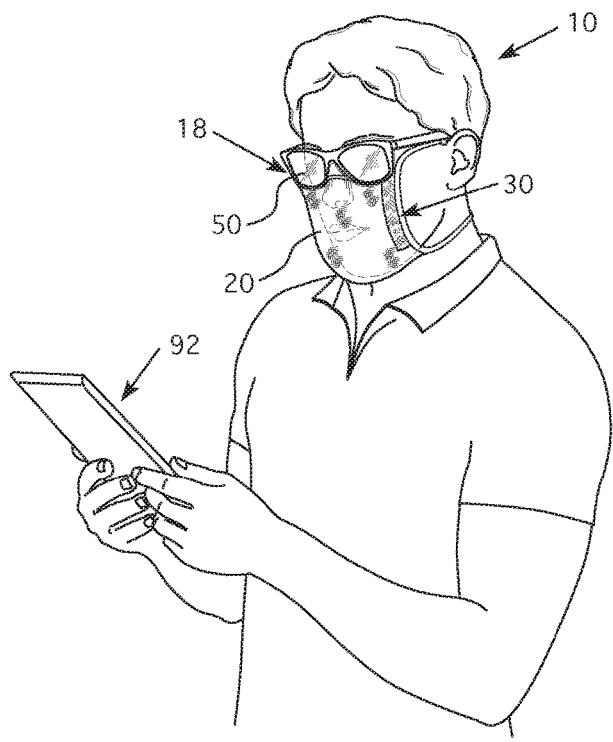
FIG. 5 illustrates a perspective view of a person wearing sunglasses with the face mask while reading and/or using an electronic peripheral.

Referring to FIG. 5, the wearer 10 may wear the face mask 20 along with the sunglasses 18 in accordance with that described earlier regarding FIG. 1 to view the electronic peripheral 92 as shown in FIG. 5. In an embodiment, the electronic peripheral 92 may not block the face mask 20 to thus allow air exhaled by the wearer 10 to flow through the vents 30 out to the exterior atmosphere 82.

Figure 6:
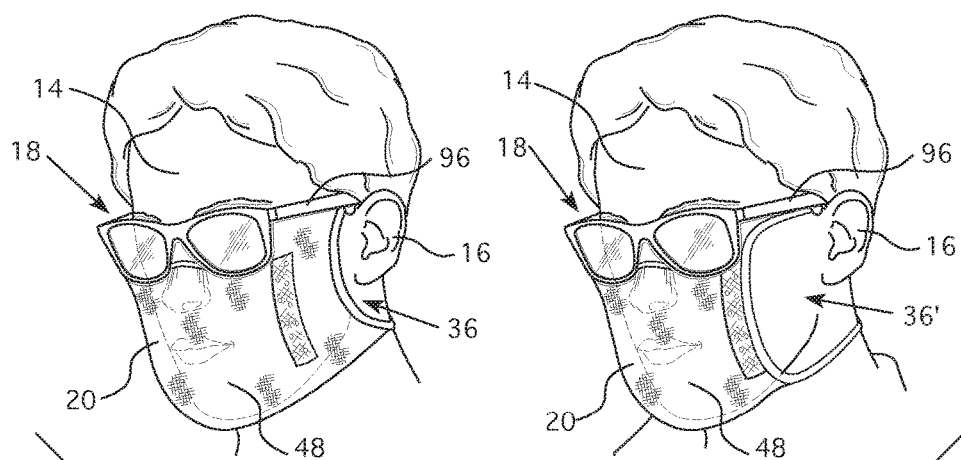
FIG. 6 illustrates two positions in which the face mask may be worn.

Referring to FIG. 6, the face mask 20 is shown positioned for placement on the face 14 of the wearer 10 in a first mode 36. The first mode 36 may place the main body 48 of the face mask 20 relatively closer to the ear 16 of the wearer, as shown. FIG. 6 also shows the face mask 20 positioned for placement on the face 14 of the wearer 10 in a second mode 36'. The second mode 36' may place the cover further away from the ear of the user.

Figure 7:
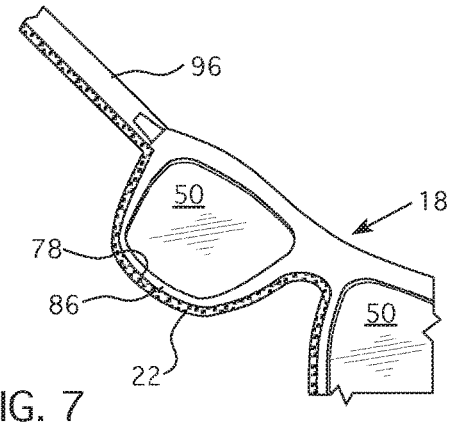
FIG. 7 illustrates a close-up inside view of the interior-facing lens surfaces of a pair of sunglasses.

Referring to FIG. 7, the sunglasses 18 are shown removed from the wearer 10. The arms 96 are shown extending from the lower frame portion 86 of sunglasses 18. The adhesive layer 78 on, around, or otherwise associated with the foam layer 22 may attach and/or adhere the face mask 20 to the sunglasses 18 along the lower frame portion 86 of the sunglasses 18. In detail, the foam layer 22 may adhere the securing strap 76 to the arms 96 of the sunglasses 18 by the adhesive layer 78 on or otherwise associated with the foam layer 22 to assist in holding the face mask 20 in place against the face 14 of the wearer 10.

Various changes and modifications to the presently preferred embodiments described herein will be apparent to those skilled in the art. Such changes and modifications may be made without departing from the spirit and scope of the present disclosure and without diminishing its attendant advantages. It is, therefore, intended that such changes and modifications be covered by the appended claims.

I claim:

1. An apparatus to prevent fogging of glasses worn by a wearer, the apparatus comprising:
    a mask made from a filtration material, the mask having a first side and a second side;
    a strap extending from the mask to hold the mask in a position on the wearer;
    a vent on each of the first side and the second side of the mask; and
    a foam layer extending across the mask and the strap to attach the mask to the glasses, the glasses having arms configured to extend from the glasses toward ears of the wearer such that the foam layer attaches the mask to the arms of the glasses.

2. The apparatus of claim 1, further comprising:
    a flap on the foam layer, wherein pulling the flap removes the foam layer from the glasses.

3. The apparatus of claim 1, further comprising:
    a binding on the mask to conform the mask to facial features of the wearer.

4. The apparatus of claim 1 wherein the mask is configured to extend toward the ears of the wearer.

5. The apparatus of claim 1 wherein a density level of interwoven fibers defining each vent is selected based on an expected respiratory rate of the wearer.

6. The apparatus of claim 1 further comprising:
    a pore on each vent, the pore being configured to direct air exhaled by the wearer away from the glasses.

7. The apparatus of claim 1, wherein the first side comprises a right side from a vantage point of looking at the wearer.

8. The apparatus of claim 1, wherein the second side comprises as a left side from a vantage point of looking at the wearer.

9. The apparatus of claim 1, wherein the first side is positioned opposite to the second side.

10. The apparatus of claim 1, further comprising:
    a top of the mask,
    a bottom of the mask, the bottom being positioned parallel and opposite to the top, wherein the top and the bottom of the face mask connect the first side to the second side to define the face mask being shaped as a rectangle.

11. A system to direct air exhaled by a user away from of glasses worn by the user, the system comprising:
    a mask contoured to conform to facial features of the user, the mask having a filtration membrane and a pair of sides connected by a top and a bottom;
    a securing strap to secure the mask to the user;
    a pair of mesh ports on the mask, each mesh port of the pair of mesh ports being located adjacent to each side of the pair of sides of the mask, the pair of mesh ports directing the air exhaled by the user away from the mask; and
    a barrier between the top of the mask and the glasses worn by the user, the barrier forming a seal between the mask and the glasses to prevent air exhaled by the user from fogging the glasses.

12. The system of claim 11 wherein a density level of fibers of each mesh port is selected in proportion to an expected respiration rate of the user.

13. The system of claim 11 further comprising:
    a tab extending from the barrier, wherein pulling the tab away from the glasses removes the barrier from the glasses.

14. The system of claim 11 further comprising:
    a ridge on the mask, wherein adjustment of the ridge fits the mask to the user.

15. The system of claim 11 wherein the mask is configured to extend toward ears of the user.

16. The system of claim 11 further comprising:
 a foam positioned between the barrier and the mask, wherein the foam provides cushioning of the glasses against the mask.

17. A method for securing a face mask against glasses worn by a wearer, the method comprising the steps of:
 positioning the face mask on the wearer;
 extending straps of the face mask around the wearer;
 adhering an adhesive foam layer of the face mask on the glasses and arms extending from the glasses toward ears of the wearer; and
 securing the face mask against the glasses.

18. The method of claim 17, further comprising the step of:
 directing air exhaled by the wearer out through the face mask.

19. The method of claim 17, further comprising the step of:
 cushioning the wearer against movement of the glasses against the face mask.

20. The method of claim 17, further comprising the step of:
 preventing fog from forming on the glasses from air exhaled by the wearer.

* * * * *